United States Patent [19]

Sugahara et al.

[11] Patent Number: 4,839,277

[45] Date of Patent: * Jun. 13, 1989

[54] METHOD FOR PURIFICATION OF HBC ANTIGEN AND METHOD FOR MEASUREMENT OF HBC ANTIBODY BY USING SAID PURIFIED HBC ANTIGEN

[75] Inventors: Keishin Sugahara; Takayuki Imamura, both of Kumamoto; Fukusaburo Hamada, Nishigoshi; Nobuya Ohtomo, Kumamoto; Haruo Fujita, Kumamoto; Kazuhide Yagami, Kumamoto, all of Japan

[73] Assignee: Juridical Foundation The Chemo-Sero-Therapeutic Research Institute, Kumamoto, Japan

[*] Notice: The portion of the term of this patent subsequent to Sep. 16, 2003 has been disclaimed.

[21] Appl. No.: 811,399

[22] Filed: Dec. 20, 1985

[30] Foreign Application Priority Data

Dec. 21, 1984 [JP] Japan .................................. 59-271432
Mar. 14, 1985 [JP] Japan .................................. 60-51678

[51] Int. Cl.$^4$ ...................... C12P 21/00; G01N 33/576
[52] U.S. Cl. .............................................. 435/7; 435/5; 435/68; 435/235; 435/239; 436/820; 935/68; 935/69
[58] Field of Search ..................... 435/5, 235, 942, 236, 435/238, 7, 239, 68; 436/820; 935/68, 69, 28

[56] References Cited

U.S. PATENT DOCUMENTS 4,547,368 10/1985 Tabor et al. ...................... 435/235
4,612,283 10/1986 Sugahara et al. ..................... 435/68
4,683,294 7/1987 Van Wijnendaele et al. ...... 530/371

FOREIGN PATENT DOCUMENTS 0118885 9/1984 European Pat. Off. .
0138167 4/1985 European Pat. Off. .

OTHER PUBLICATIONS

Hoofnagle et al., *N. Engl. J. Med.*, 298:1379–1383, 1978.
Heftmann, E. (ed.), "Chromatography of Proteins," *Chromatography*, chapter 15, pp. 378–427 (1961).
Pharmacia Fine Chemicals booklet "Ion Exchange Chromatography Principles and Methods," pp. 27–54 (3/1980).
Stahl et al., "Hepatitis B Virus Core Antigen: Synthesis in *Escherichia Coli* and Application in Diagnosis," PNAS, vol. 79, pp. 1606–1610, Mar. 1982.

Primary Examiner—Robert J. Warden
Assistant Examiner—Carol A. Spiegel
Attorney, Agent, or Firm—Wegner & Bretschneider

[57] ABSTRACT

A method for the purification of HBc antigen, particularly HBc antigen produced by recombinant organisms by means of DNA recombination technique, which comprises subjecting a solution containing HBc antigen to acid-treatment, wherein the solution containing HBc antigen is acidified to a pH range of not higher than 6 by adding an acid and then resulting precipitates of lipid and contaminant proteins are removed, and then subjecting the acid-treated solution containing HBc antigen to an ion exchange chromatography with an anion exchanger, and a method for measuring HBc antibody by using said purified HBc antigen in a passive hemagglutination method, EIA method or RIA method.

11 Claims, 3 Drawing Sheets

METHOD FOR PURIFICATION OF HBC ANTIGEN AND METHOD FOR MEASUREMENT OF HBC ANTIBODY BY USING SAID PURIFIED HBC ANTIGEN

The present invention relates to a method for the purification of hepatitis B virus core antigen (hereinafter, referred to "HBc antigen"), and a method for the measurement of hepatitis B Virus Core antibody HBc antibody using said purified HBc antigen. More particularly, it relates to a method for the purification of HBc antigen produced by recombinant organisms by means of DNA recombination technique, and a method for the measurement of HBc antibody by using said highly purified HBc antigen.

TECHNICAL BACKGROUND AND TECHNICAL FIELD

Hepatitis B is a disease which is induced by a hepatitis B virus (hereinafter, referred to as "HBV") and includes immunologically and clinically very serious problems for which there is not effective therapeutic method. This disease has been observed worldwide, particularly in Asian and African areas, and hence, it has been desired to find an effective prophylactic and therapeutic method therefor.

HBV is a spherical virus having a diameter of 42 nm and consists of a surface and a core which have separate antigenicity and are called HBs antigen and HBc antigen, respectively. It is also known that there is another antigen of HBV, i.e. HBe antigen reported by Magnius et al. [cf. J. Immunology, 160, 1017 (1972)].

For prophylaxis of this disease, it is very important to discover the infection with HBV at an early stage. For the diagnosis of the infection with HBV, there are utilized antigen-antibody systems such as HBs antigen-antibody, HBc antigen-antibody and HBe antigen-antibody. Among these, except HBc antigen which is almost not present in blood flow, five antigens and antibodies can be measured by immunological measurement such as passive hemagglutination (hereinafter, referred to "PHA"), reverse-passive hemagglutination (hereinafter, referred to "rPHA"), enzyme immunoassay (hereinafter, referred to "EIA") and radioimmunoassay (hereinafter, referred to "RIA"). In particular, HBe antigen is very important as an index for diagnosis of infection with HBV. It is known that HBe is a derivative of a HBc antigen protein and hence is dominated by the HBc gene. That is, when the product is associated to form a completely spherical particle, it shows an antigenicity as HBc, but on the other hand, when the product is dissociated, it shows other antigenicity than HBe [cf. KanTan-Sui (Liver-Gall-Pancreas), 10, 7-13 (1985)]. It is also known that HBc antibody shows, in blood, some behavior parallel to the amount of HBc antigen which is the main body of HBV within the liver. It is very important to measure HBc antibody in order to know whether HBV increasing or decreasing within the liver, because it can not be detected by the measurement of HBs antigen, HBe antigen or HBe antibody.

For the measurement of HBc antibody, a pure HBc antigen is necessary. However, HBV antigen is not present in blood flow as HBc antigen per se and HBc antigen must be isolated from human liver. Besides, it is very difficult to isolate from human liver, and the isolation is accompanied with some danger of infection. Thus, since the isolation of HBc antigen is restricted, the human-origin HBc antigen has merely been used in research laboratories for measuring HBc antibody.

PRIOR ART

Known methods for the purification of liver-origin HBc antigen are a combination of a density gradient centrifugation and a gel filtration [cf. Budkowaska, A. et al., J. Immunology, 118, 1300 (1977) and Ohori, H. et al., Intervirology, 13, 74 (1980)]and a density gradient centrifugation [cf. Feitelson, M.A. et al., J. Virology, 43, 687 (1982)]. It is also known to obtain blood-origin HBc antigen from infectious Dane particles of HBV as a whole by centrifugation, fracturing the virus particles with surfactant, etc., and isolating the antigen by a density gradient centrifugation [cf. Takahashi, K. et al., J. Immunology, 122, 275 (1979), etc.]Moreover, it is known that HBc antigen obtained by expressing in cells of E. coli by DNA recombination technique can be purified by a density gradient centrifugation [cf. Roggendorf, M. et al., J. Virological Methods, 6, 61 (1983), etc.]. However, these methods still can not remove the problems in the purification of HBc antigen obtained from recombinant organisms and are hardly used as an industrial purification method.

In case of purification of HBc antigen obtained from recombinant organisms, there are some problems with contaminated components in the starting materials, such as recombinant-origin proteins, lipids and other components, which are essentially different from the contaminants in case of HBc antigen obtained from human liver and human blood not only in the quality but also in the quantity, and hence, it cannot be sufficiently purified by conventional purification methods. Even by the above method Roggendorf et al. wherein it has been tried to purify recombinant-origin HBc antigen, it has merely been purified in such a degree that it can be analyzed, but is cannot give a highly pure product that can be used as a diagnostic product or a vaccine. Besides, there has never been a study of the yield thereof. Thus, such a method cannot be used for the purification of a recombinant-origin HBc antigen on an industrial scale.

Recently, there has been on the market a PHA reagent for detaching HBc antibody which is prepared by expressing HBc antigen in E. coli by utilizing DNA recombination technique and then sensitizing the obtained antigen to sheep erythrocyte [cf. Clinical Test, 28, 1227-1232 (1984)]. This PHA reagent is clinically useful with good effect, but it is still insufficient in sensitivity.

BRIEF DESCRIPTION OF THE INVENTION

By extensive studies on a safe and practical method for the purification of recombinant-origin HBc antigen by the present inventors, it has now been found that when the HBc antigen material obtained from culture of recombinant organisms which contains recombinant-origin contaminants is made acidic with an acid, the contaminant lipids and proteins which interfere with chromatography of the HBc antigen are precipitated and can be separated from HBc antigen, and that the HBc antigen thus separated can be easily and highly purified by subjecting to an ion exchange chromatography with an anion exchanger, optionally followed by a density gradient centrifugation, and further that the HBc antigen thus purified is useful for the measurement of HBc antibody.

An object of the present invention is to provide a method for purification of HBc antigen stably and on an industrial scale to give a safe and cheap HBc antigen. Another object of the invention is to provide a purification method of HBc antigen obtained from recombinant organisms by DNA recombination technique in a high purity and on a large scale. A further object of the invention is to provide a method for the measurement of HBc antibody by using the highly purified HBc antigen. These and other objects and advantages of the invention will be apparent to those skilled in the art from the following description.

DETAILED DESCRIPTION OF THE INVENTION

Purification of HBc Antigen

Figure 1:
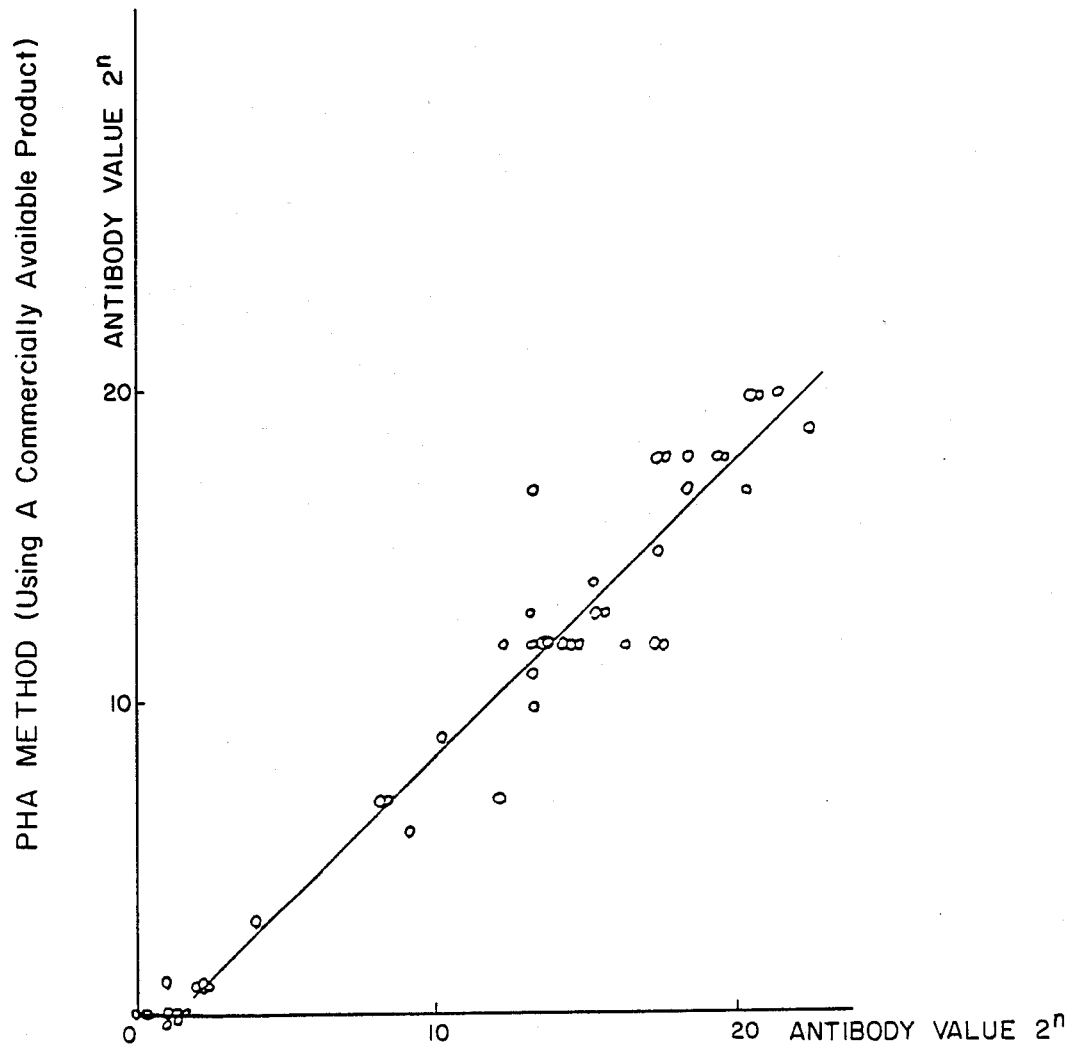
FIG. 1 shows a correlation between the method of measuring HBc antibody by the present invention and that of the conventional PHA method.

The method for the purification of HBc antigen, particularly HBc antigen produced by recombinant organisms by DNA recombination technique, of the present invention is characteristic in that a starting material containing HBc antigen obtained from a culture of a recombinant organism and also containing recombinant-origin components is converted to an acidic pH by adding thereto an acid, thereby precipitating and removing most of the lipids and contaminant proteins which bar subsequent chromatography, and then directly or after subject to purification by salting out with ammonium sulfate or being concentrated, subjecting to an ion exchange chromatography with an anion exchanger.

The starting HBc antigen material used in the present invention is obtained by culturing a recombinant organisms obtained by a DNA recombination technique which is capable of producing HBc antigen, for instance recombinant E. coli or yeasts in an appropriate medium under suitable culture conditions to produce and accumulate HBc antigen in the medium, and then roughly extracting the HBc from the culture by a conventional method.

Examples of the recombinant organisms being capable of producing HBc antigen are published by the present inventors [cf. "Saibo Kogaku" (Cell Technology), 3, No. 4, 367–370 1984, and 31th Meeting of Japan Virus Association, at Osaka, 1983, Subject No. 2036], and can be prepared as follows.

Plasmid pHBV containing whole DNA sequences of HBV (cf. Japanese Patent First Publication No. 36699/1984 and EP-A-No. 0103201) is digested with a restriction enzyme (e.g. Rsa I), and the resulting DNA sequence including HBc gene is inserted into plasmid pACYC177 at Xho I site thereof to give a recombinant plasmid pAHBc. The plasmid pAHBc is digested with a restriction enzyme Xho I, and the resulting DNA sequence including HBc gene is inserted into a shuttle vector pAM 82 (cf. Japanese Patent First Publication No. 36699/1984 and EP-A-No. 0103201) at Xho I site thereof to give plasmid pAC 301 suitable for expressing HBc.

Alternatively, the above plasmid pAHBc is partially digested with a restriction enzyme Xho I to remove pre-C region at 5'-end thereof and the resulting plasmid is treated with $T_4$ DNA synthetase to convert the cohesive end thereof into the flush end, and thereafter, Xho I site is added to the EcoRI site thereof with a EcoRI linker. There is elected a plasmid wherein Xho I site at the 5' side of the HBc gene is converted into a EcoRI site. The thus obtained plasmid pHBc 1 is digested with EcoRI and further with BAL 31 and is attached with Sal I linker, and then, the plasmid is digested with restriction enzymes Xho I and Sal I to give an HBc gene fragment where the pre-C region of about 600 base pair is removed. The thus obtained fragment is inserted into shuttle vector pAm 81 at Sal I site thereof (cf. Japanese Patent First Publication No. 356699/1984 and EP-A-No. 0103201) to give a vector pAC 701 suitable for expressing HBc.

By using the above vector suitable for expressing HBc, a yeast Saccharomyces cerevisiae AH 22 [a leu2 his4 can1 (Cir+)](which has been deposited at Fermentation Research Industrial Science and Technology, Japan under Budapest Treaty as "FERM BP-312") is transformed in the same manner as described in the above mentioned Japanese patent application and European patent application to give a transformed yeast Saccharomyces cerevisiae pAC 301 and Saccharomyces cerevisiae pA 701, which are capable of producing HBc antigen. These transformed yeasts are cultured in a usual manner to give the desired culture of recombinant organisms.

Extraction of HBc antigen from the culture can be carried out by separating cells from the culture by centrifugation, and fracturing the cells in an appropriate buffer solution. The fracturing is carried out by conventional methods such as ultrasonic fracture, glass beads fracture, Manton-Gaulin fracture, or enzymatic dissolution of the cell walls, followed by fracturing the resulting spheroplast with a detergent. The fractured cells are subjected to centrifugation at a slow speed to remove the cell wall pieces, and further optionally to filtering with a membrane filter to give the desired starting HBc antigen-containing material.

The starting HBc antigen-containing material is made acidic by adding thereto an acid, and thereby, most of the lipids and contaminants proteins which bar the subsequent chromatography are removed in the form of precipitates, followed by ion exchange chromatography with an anion exchanger and further optionally to density gradient centrifugation to give the desired highly purified HBc antigen.

The acids used in the above acidification step include inorganic acids (e.g. hydrochloric acid, sulfuric acid, phosphoric acid, etc.) and organic acids (e.g. acetic acid, oxalic acid, etc.). The acidification with an acid is effected so as to regulate the pH of the material in the range of not higher than 6, preferably in the range of pH 5.0 to 5.5. The acidification treatment is usually carried out at a temperature not higher than 20° C., preferably in the range of 4 to 10° C. After the regulation of pH, the resulting precipitates are separated by centrifugation, and the supernatant containing HBc antigen is obtained.

The HBc antigen-containing solution thus obtained is optionally subjected to purification by salting out with ammonium sulfate and/or to concentration. That is, the supernatant containing HBc antigen is adjusted to pH 6.0 to 8.0 by adding thereto aqueous ammonia having an appropriate concentration, and the resulting precipitates of HBc antigen are separated from the supernatant by centrifugation. The precipitates thus obtained are dissolved in an appropriate neutral buffer solution having an ion strength of at least 0.001 (e.g. 0.1 M phosphate buffer) and subjected to dialysis with the same buffer as above to give a material for subjecting to a chromatography with an anion exchanger.

In case of subjecting to salting out with ammonium sulfate, the HBc antigen-containing supernatant is neutralized, i.e. adjusted to about pH 7.0, with aqueous ammonia and then diluted with the same buffer as above or subjected to dialysis with the same buffer as above to give the desired material for chromatography.

The anion exchanger used for the chromatography is most preferably an anion exchanger having a diethylaminoethyl group as a functional group, and includes commercially available products, such as DEAE-Sephadex A-25, DEAE-Sephadex A-50, DEAE-Sepharose and DEAE-Sephacel (manufactured by Pharmacia Fine Chemicals), DEAE Bio-Gel A and Cellex D (manufactured by Bio-Rad Co.), and DEAE-Cellulofine (manufactured by Seikagaku Kogyo K.K., Japan). The ion exchange chromatography with these anion exchangers is carried out as follows.

Adsorption of HBc antigen with anion exchanger is carried out by a batch method or a column method. In case of a column method, a column packed with an anion exchanger is equilibrated by passing through the same buffer solution as used in the above preparation of the material for chromatography, and then, the HBc antigen-containing solution is passed through, by which HBc antigen is adsorbed onto the anion exchanger but the recombinant-origin contaminants are passed without being absorbed. Thereafter, the column is washed with the same buffer as used for the equilibration to wash out the contaminants, and then, the column is subjected to the subsequent elution step.

In the case of a batch method, an anion exchanger equilibrated with a buffer is added to the HBc antigen-containing solution, and the mixture is stirred at a low speed for about 0.5 to 2 hours to make adsorb HBc antigen onto the exchanger. After the adsorption, the anion exchanger is collected on a filter, and the exchanger gel thus obtained is washed with the same buffer as used for equilibration, followed by filtration. This treatment is repeated several time, and the resulting HBc antigen-adsorbed exchanger is subjected to the subsequent elution step. In this batch method, the HBc antigen-adsorbed exchanger is preferably packed in a column and then subjected to the elution.

The elution is carried out by a stepwise elution or a concentration gradient elution with a buffer solution having a higher ion strength than that of the buffer for equilibration, i.e. having an ion strength of about 0.01 to 0.5, and thereby HBc antigen is separated from the remaining adsorbed contaminants to give an HBc antigen-containing fraction. The concentration gradient elution can be carried out by suing sodium chloride-added 0.01 M phosphate buffer having a concentration gradient of 0.01→0.5 M or any other buffer solutions having an appropriate concentration gradient effective for separation of HBc antigen from the contaminants. The stepwise elution can be carried out by passing through a buffer solution having an ion strength which is effective for elution of only contaminants, followed by passing through a buffer having a stronger ion strength, by which a fraction containing highly purified HBc antigen is obtained.

The HBc antigen thus purified may optionally be subjected to further purification methods, such as sucrose step gradient centrifugation or sucrose linear gradient centrifugation, followed by precipitation equilibrium centrifugation or linear gradient centrifugation with cesium chloride, by which a further highly purified HBc antigen can be obtained.

In order to enhance the degree of purity of the HBc antigen in the ion exchange chromatography or to enhance the degree of purity of HBc antigen in the fractions pooled in a wide range in the chromatography, the ion exchange chromatography is preferably combined with a chromatography with hydroxyapatite. The hydroxyapatite is a gel for affinity chromatography which is composed of calcium phosphate and includes a commercially available hydroxyapatite (manufactured by Seikagaku Kogyo K.K. and (ALBIOCHEM-BEHRING) and hydroxylapatite (manufactured by BioRad Co.). That is, the HBc antigen-containing fraction is dialyzed against an appropriate neutral buffer having an ion strength of about 0.01 to 0.2 (e.g. 0.1 M phosphate buffer) or diluted with the same buffer as above, and then equilibrated with the same buffer as above, and the resulting solution is passed through a hydroxyapatite column, whereby the HBc antigen is not adsorbed but is in the passed through fraction.

The present inventors have tried to purify the recombinant-origin HBc antigen by using various conventional gels for chromatography, such as CM cellulose, CM Sepharose, cellulose phosphate, etc. instead of the anion exchanger, but could not obtain the desired purification effect.

MEASUREMENT OF HB ANTIBODY

The HBc antigen purified above can be used for various immunological measurements of HBc antibody, such as the PHA method (passive hemagglutination method), r-PHA method (reverse-passive hemagglutination method), EIA method (enzyme immunoassay method), and RIA method (radioimmunoassay method) as follows.

(i) Measurement by PHA method:

The HBc antigen purified above is sensitized to a carrier with tannic acid or the like to prepare a sensitized carrier for passive carrier agglutination. The carrier includes mammalian or bird erythrocytes immobilized with formalin or glutaraldehyde or artificial carriers. The artificial carriers include latex (polystyrene) particles, gelatin, epoxy resins, cellulose resins, activated carbon, and the like. The antigen-sensitized carries thus prepared show an agglutination image in the presence of an antibody against a certain amount of an antigen. Accordingly, the HBc antibody can be measured by evaluating the agglutination image.

The antigen-sensitized carriers can be kept in a phosphate-buffered sodium chloride solution (PBS) containing 1% normal rabbit serum (NRS) and 0.1% sodium nitride (azide), and can be used when desired.

(ii) Measurement by EIA Method or RIA method:

In the case of the measurement of EIA method or RIA method, there are used as the carrier polystyrene beads, polystyrene tube, a plain bottom plate for ELISA (Nunc-Immuno Plate, manufactured by Nunc & Co., and FLAT BOTTOM MICROELISA® PLATES, manufactured by Immulon Dinateck Co.).

(ii)-1 Sensitization

The sensitization with antigen to a solid carrier is usually carried out by a non-specific adsorption or with a crosslinking agent such as glutaraldehyde.

[Non-specific adsorption method]

In the case of a non-specific adsorption method, the HBc antigen is added to a buffer having pH 9–10 (e.g. carbonate buffer) to prepare an HBc antigen solution containing an appropriate amount of HBc, and the solid carrier (in case of beads) is dipped in the antigen solution for a sufficient time, or the antigen solution is entered into wells or a tube of the solid carrier and allowed to stand for a sufficient time, by which the antigen is adsorbed onto the solid carrier. The time for dipping or allowing to stand is preferably about 2 hours at 37° C. or overnight at 4° C. The antigen-adsorbed solid carrier is treated with PBS containing 1% bovine serum albumin (BSA) in order to decrease non-specific reaction.

[Method by using crosslinking agent]

In the case of using a crosslinking agent such as glutaraldehyde, the solid carrier is treated with a buffer (pH 9–10) (e.g. carbonate buffer) containing a few or several & of a crosslinking agent (e.g. glutaraldehyde) for a sufficient time. The time is preferably about 2 hours at 37° C. or overnight at 4° C. It is sensitized with the antigen and BSA like the above.

(ii)-2 Method for measurement

The measurement of HBc antibody with the solid carrier prepared above is usually carried out by a non-competition method or a competition method.

In case of EIA method:

Non-competition method:

In case of a non-competition method, the solid carrier is reacted with the test sample and then is washed with a buffer. Detection of IgG reacted with HBc antigen is carried out by reacting with anti-human IgG antibody or protein A which is labelled with an enzyme (e.g. peroxidase) (in case of human-origin test sample). After washing, to the reaction mixture is added a substrate which can become colored by the labelling enzyme, and thereafter, an appropriate reaction stopper (e.g. sulfuric acid) is added to the reaction mixture to stop the reaction, and then, the degree of color of the reaction mixture is measured with a photometer.

Competition method:

In case of a competition method, the reaction of the solid carrier and the test sample is carried out in the presence of a fixed amount of an enzyme-labelled anti-HBc antibody, whereby the anti-HBc antibody contained in the test sample competes with the enzyme-labelled anti-HBc antibody for the antigen immobilized onto the solid carrier. After the reaction, the reaction mixture is colored like above, by which the degree of color is decreased in proportion to the amount of anti-HBc antibody contained in the test sample.

In case of RIA method:

The RIA method can be carried out by the same principle as in the EIA method, except hat a radioisotopelabelled anti-human IgG antibody or a radioisotope-labelled protein A is used instead of an enzyme-labelled anti-human IgG antibody, and a radioisotope-labelled anti-HBc antibody is used instead of an enzyme-labelled anti-HBc antibody, and further the radioactivity is measured with an appropriate device which can detect the radioisotope used for labelling.

The present invention is illustrated by the following Examples but should not be construed to be limited thereto.

Examples of the purification of HBc antigen are illustrated below.

EXAMPLE 1

A recombinant yeast, Saccharomyces cerevisiae AH 22 pho 80/pAC 701 is cultured and the cells are collected by centrifugation. To the cells (about 600 g) is added 50 mM phosphate buffer (pH 7.2, 3 liters), and the mixture is treated with a Manton-Gaulin fracturing machine under a pressure of 600 kg/cm$^2$ for about 3 hours to fracture the cells. The fractured cells are centrifuged to remove coarse pieces of the fractured cells to give a crude extract of HBc antigen which has an HBe antigen activity of about 30,000 cpm [measured after a 400-fold dilution with RIA kit-HBe RIA kit (manufactured by Abbott, U.S.A.)].

The crude extract is adjusted to pH 5.4 by adding thereto dropwise acetic acid, while checking the pH with a pH meter. After stirring the mixture at 4° C. for about 30 minutes, the precipitates are removed by centrifugation. While maintaining the supernatant at pH 6.5 by adding thereto aqueous ammonia, ammonium sulfate is gradually added until the final concentration of 2.5 M. The mixture is stirred at 4° C. for 30 minutes and allowed to stand overnight. The resulting precipitates containing HBc antigen are separated by centrifugation.

The precipitates thus obtained are suspended in 10 mM phosphate buffer-50 mM potassium chloride (pH 7.3, about 300 ml) and the mixture is dialyzed against the same buffer as above (about 100 folds by volume) with a tube for dialysis. After the dialysis, the solution is diluted about 3 fold with a 10 mM phosphate buffer-50 mM potassium chloride (pH 7.3). The diluted solution is added to a column packed with DEAE-cellulose gel (gel amount: about 1 liter) which is previously equilibrated with the same buffer as above, by which HBc antigen is adsorbed on the gel. The column is washed well with the same buffer as used for equilibration, and then subjected to elution by passing through 50 mM→500 mM potassium chloride concentration gradient phosphate buffer, and HBc antigen-containing fractions are collected.

The collected fractions are pooled and concentrated with an ultrafiltration concentrator Amicon TCF-10 (manufactured by Amicon Co.). In an ultracentrifugation tube there are piled up 60% sucrose solution, 20% sucrose solution and the concentrated HBc solution in an amount of 10 ml, 35 ml and 35 ml, respectively, and the tube is subjected to ultrafiltration at 30,000 r.p.m., at 4° C. for 19 hours, and thereby, HBc antigen is concentrated and purified at the interface of the sucrose solutions.

The HBc antigen fraction thus obtained is dialyzed against a mixture of 50 mM Tris-HCl, 150 mM sodium chloride and 1mM EDTA (pH 7.5), and thereto is added cesium chloride in a concentration of 1.32 g/ml, and the mixture is ultracentrifuged at 30,000 r.p.m., at 4° C. for 60 hours to give a purified HBc antigen.

The recovery rate and purification degree of HBc in each step are shown in Table 1.

TABLE 1

| Steps | Recovery rate | Purification degree |
|---|---|---|
| Crude extract | 100 | 1 |
| Supernatant after | 92 | 2 |

TABLE 1-continued

| Steps | Recovery rate | Purification degree |
|---|---|---|
| acid-treatment | | |
| Precipitate with ammonium sulfate | 84 | 2.7 |
| DEAE-cellulose | 39 | 39 |
| Ultracentrifugation with sucrose | 30 | 420 |
| Ultracentrifugation with CsCl | 14 | 1230 |

EXAMPLE 2

In the same manner as described in Example 1, HBc antigen is concentrated and purified at the interface of sucrose solutions.

The HBc antigen-containing fractions thus obtained are dialyzed against 0.1 M phosphate buffer (pH 7.3), and then passed through a hydroxyapatite column which is previously equilibrated with the same buffer as above. The fractions pass through which contain HBc antigen without being adsorbed are pooled, and to the pooled fraction is added cesium chloride in a concentration of 1.32 g/ml, and the mixture is ultracentrifuged at 30,000 r.p.m., at 4° C. for 60 hours to give a purified HBc antigen.

The recovery rate and purification degree in each step are shown in Table 2.

TABLE 2

| Steps | Recovery rate | Purification degree |
|---|---|---|
| Crude extract | 100 | 1 |
| Supernatant after acid-treatment | 92 | 2 |
| Precipitate with ammonium sulfate | 84 | 2.7 |
| DEAE-cellulose | 45 | 25 |
| Ultracentrifugation with sucrose | 35 | 245 |
| Treatment with hydroxyapatite | 24 | 683 |
| Ultracentrifugation with CsCl | 17 | 1230 |

EXAMPLE 3

To the cells (100 g) obtained by culturing a recombinant yeast, *Saccharomyces cerevisiae* AH 22 pho 80/pAC 701 and centrifuging the culture is added 50 mM phosphate buffer (pH 7.2, 500 ml), and the mixture is subjected to an ultrasonic treatment at 4° C. for about 90 minutes to fracture the cells. The fractured cells are centrifuged in the same manner as described in Example 1 to remove the coarse pieces of cells, and thereby, a crude extract of HBc antigen is obtained.

The crude extract is purified in the same manner as described in Example 1 to give a purified HBc antigen. The recovery rate and purification degree of HBc antigen in each step are shown in Table 3.

TABLE 3

| Steps | Recovery rate | Purification degree |
|---|---|---|
| Crude extract | 100 | 1 |
| Supernatant after acid-treatment | 92 | 2 |
| Precipitate with ammonium sulfate | 85 | 2.5 |
| DEAE-cellulose | 43 | 41 |
| Ultracentrifugation with sucrose | 32 | 390 |
| Ultracentrifugation | 16 | 1100 |

TABLE 3-continued

| Steps | Recovery rate | Purification degree |
|---|---|---|
| with CsCl | | |

EXAMPLE 4

To cells (200 g) obtained by culturing a recombinant yeast Saccharomyces cerevisiae AH 22 pho 80/pAC 701 and centrifuging the culture is added 50 mM potassium phosphate buffer (pH 7.2, 600 ml) which contains 100 μg/ml of zymoliase (manufactured by Seikagaku Kogyo K.K., Japan), and the mixture is stirred at 30° C. for 30 minutes and then centrifuged to give precipitates of spheroplast of yeast. To the precipitates is added 0.1% Triton X-100-containing 50 mM phosphate buffer (pH 7.2, 200 ml), and the mixture is stirred at room temperature for 1 hour to give a solution of lysed cells. The solution is centrifuged to remove coarse pieces of the fractured cells, by which a crude extract is obtained.

To the crude extract is added 40% (w/w) polyethylene glycol 6,000 in a final concentration of 3%, and the mixture is stirred at 4° C. for 1 hour, and then centrifuged to remove the supernatant. The precipitates are suspended in 10 mM potassium phosphate buffer-50 mM potassium chloride (pH 7.2, 80 ml). The suspension is subjected to ultrasonic treatment for 5 minutes to solubilize. The resulting solution is dialyzed against 10mM potassium phosphate buffer-50 mM KCl (pH 7.2) at 4° C. overnight, and is added to DEAE-cellulose. The mixture is treated in the same manner as described in Example 1 to prepare a purified HBc antigen. The recovery rate and purification degree of HBc antigen in each step are shown in Table 4.

TABLE 4

| Steps | Recovery rate | Purification degree |
|---|---|---|
| Crude extract | 100 | 1 |
| Precipitation with PEG | 90 | 2.4 |
| DEAE-cellulose | 39 | 38 |
| Ultracentrifugation with sucrose | 26 | 410 |
| Ultracentrifugation with CsCl | 12 | 1200 |

Examples of the measurement of HBc antibody are illustrated below.

EXAMPLE 5

Immobilization of sheep erythrocytes

A blood (100 ml) of sheep is mixed with Alsever's solution (100 ml), and the mixture is filtered with cotton gauze, and the concentration of erythrocytes is measured by hematocrit.

The precipitates obtained by the above filtration are washed with a physiological saline solution 5 times and treated in the same manner as described by Abram B. Stavitsky [cf. Methods in Immunology and Immunochemistry, IV, 33-34 (1977), ed. by Williams, Chase, Academic Press, New York]to prepare formalin-immobilized sheep erythrocytes.

That is, to the washed precipitates of erythrocyte obtained above is added an 8 fold amount of a cold 3% solution of formaldehyde in a physiological saline solution, and the mixture is slowly stirred at 4° C. for 24 hours. To the mixture is further added a 2 fold amount of a cold 37% formaldehyde solution, and the mixture is stirred at 4° C. for 24 hours. The mixture is filtered through a cotton gauze, and the erythrocytes are washed with a physiological saline solution 8 times, and suspended in PBS in a concentration of 2.5%, and thereto is added 1/100 amount of sodium nitride. The mixture is preserved at 4° C.

Preparation of sensitized erythrocytes:

The immobilized sheep erythrocytes prepared above are washed with PBS two times, and are suspended in PBS in a concentration of erythrocyte of 2.5%. The mixture is treated in the same manner as described in the abovementioned literature, "Methods in Immunology and Immunochemistry", IV, 36, to sensitize the antigen. That is, the 2.5% sheep erythrocyte mixture (30 ml) is mixed with the same volume of a 0.0005% tannic acid solution in PBS, and the mixture is reacted at 37° C. for 45 minutes. The reaction mixture is washed with PBS three times, and is suspended in PBS in a concentration of erythrocyte of 2.5%.

Separately, the HBc antigen purified in Example 1 is diluted with PBS so as to be at a concentration of antigen in a range of 0.005-0.2 at $OD_{280}$. The diluted HBc antigen solution is mixed with the same amount of the above tannic acid-treated erythrocytes, and the mixture is reacted at 37° C. for 30 minutes to sensitize well. The erythrocytes thus treated are suspended in PBS containing 1% normal rabbit blood serum (NRS) and 0.1% sodium nitrite so as to produce a concentration of erythrocyte of 0.75%, and thereby, sensitized erythrocytes (100 ml) are obtained.

Measurement of HBc antibody by passive hemagglutination:

Human sera (45 samples) were continuously diluted twofolds in a microtiter plate. The dilution was carried out with 1% NRS-containing PBS. After the dilution, the sensitized erythrocytes were added thereto, and the mixture was allowed to stand at room temperature for 2 hours, and the antibody value was measured by the agglutination pattern. The results are shown in Table 5, wherein the data obtained by PHA method (using a commercially available E. coli-origin HBc antigen) and RIA method (using a commercially available human-origin HBc antigen) are used for comparison purpose.

In case of the PHA method of the present invention and the PHA method using a commercially available E. coli-origin HBc antigen, the antibody value is shown by 'n' in $2^n$ in the table, and when n is 5 or more, it is evaluated that it is positive, and when n is less than 5, it is evaluated that it is negative. In the case of the RIA method using a commercially available human-origin HBc antigen, the valve is expressed by the inhibition rate (%), and when the ratio is 70% of more, it is evaluated that it is positive, and when the value is less than 30%, it is evaluated that it is negative.

As a result, the evaluation was completely the same for the method of the present invention and the PHA method using E. coli-origin HBc antigen and also for the present invention and the RIA method using human-origin HBc antigen.

Figure 2:
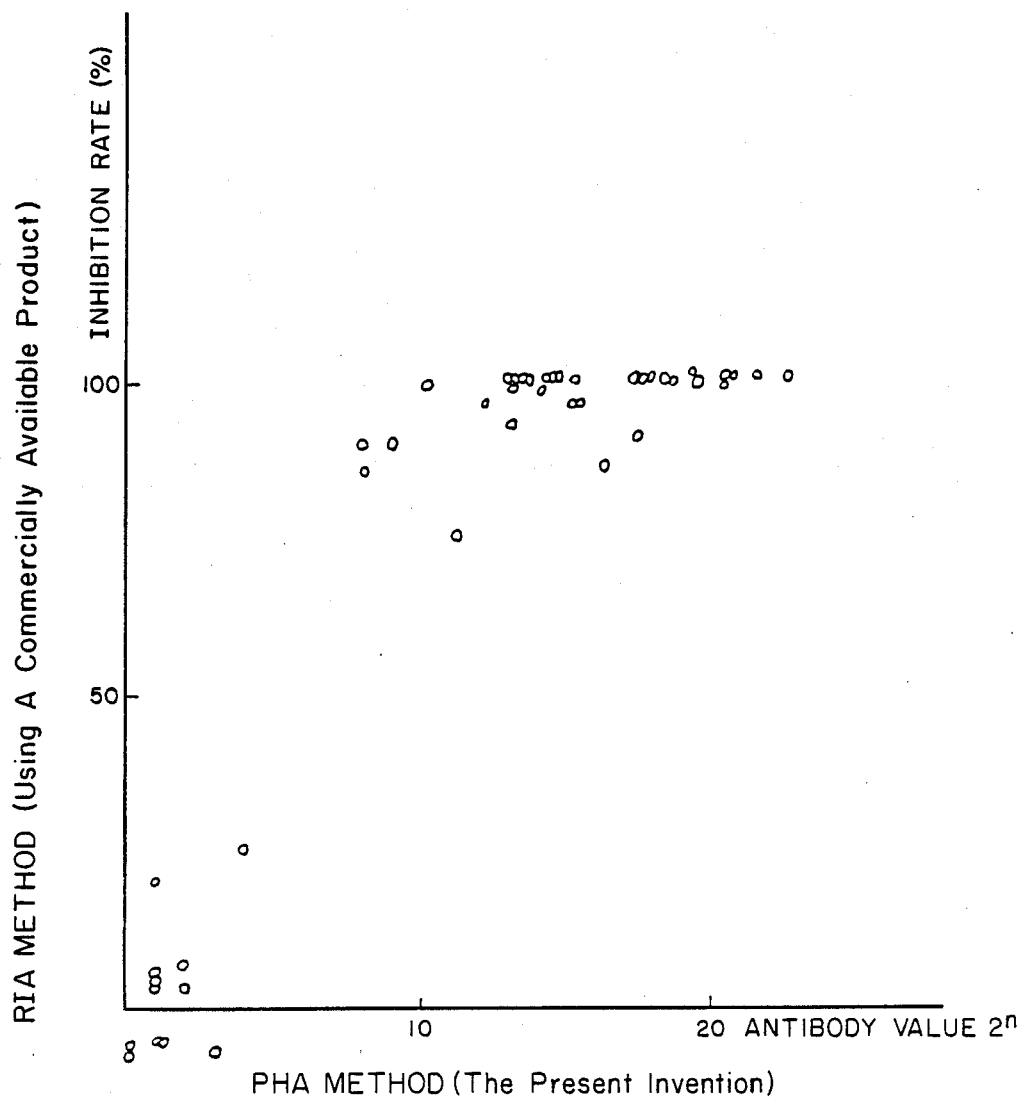
FIG. 2 shows a correlation between inhibition rate (%) in the method of the present invention and that of the conventional PHA method.

Besides the antibody value in the present invention was well correlative with that of the PHA method using E. coli-origin HBc antigen. Moreover, it was found that the sensitivity of the present invention is two times higher than that of the PHA method using E. coli-origin HBc antigen. The data are shown in the accompanying FIG. 1. Besides, the correlative figure between the present invention and the RIA method using human-origin HBc antigen is also shown in the accompanying FIG. 2.

TABLE 5

(Measurement of HBc antibody by passive hemagglutination)

| Run No. of test sample | PHA method by the present invention $2^n$ | Evaluation | PHA method using E. coli-orgin HBc antigen $2^n$ | Evaluation | RIA method using human-origin HBc antigen Inhibition rate (%) | Evaluation |
|---|---|---|---|---|---|---|
| 1 | 1 | — | <1 | — | 20.0 | — |
| 2 | 1 | — | <1 | — | 2.1 | — |
| 3 | 2 | — | 1 | — | −8.5 | — |
| 4 | <1 | — | <1 | — | −7.0 | — |
| 5 | <1 | — | <1 | — | −9.4 | — |
| 6 | 1 | — | <1 | — | 4.1 | — |
| 7 | 2 | — | 1 | — | 5.1 | — |
| 8 | 1 | — | <1 | — | −6.7 | — |
| 9 | 2 | — | 1 | — | 2.6 | — |
| 10 | 1 | — | 1 | — | −6.8 | — |
| 11 | 4 | — | 3 | — | 25.3 | — |
| 12 | 1 | — | <1 | — | 3.4 | — |
| 13 | 10 | + | 9 | + | 99.7 | + |
| 14 | 8 | + | 7 | + | 90.9 | + |
| 15 | 9 | + | 6 | + | 90.5 | + |
| 16 | 17 | + | 12 | + | 100.4 | + |
| 17 | 8 | + | 7 | + | 87.5 | + |
| 18 | 14 | + | 12 | + | 100.5 | + |
| 19 | 13 | + | 12 | + | 100.7 | + |
| 20 | 14 | + | 12 | + | 100.0 | + |
| 21 | 13 | + | 12 | + | 100.6 | + |
| 22 | 18 | + | 18 | + | 100.8 | + |
| 23 | 19 | + | 18 | + | 101.0 | + |
| 24 | 14 | + | 12 | + | 98.3 | + |
| 25 | 11 | + | 7 | + | 75.0 | + |
| 26 | 17 | + | 18 | + | 100.7 | + |
| 27 | 20 | + | 20 | + | 99.9 | + |
| 28 | 20 | + | 20 | + | 101.0 | + |
| 29 | 13 | + | 13 | + | 100.6 | + |
| 30 | 21 | + | 20 | + | 101.4 | + |
| 31 | 13 | + | 12 | + | 100.3 | + |
| 32 | 15 | + | 14 | + | 99.9 | + |
| 33 | 17 | + | 15 | + | 100.9 | + |
| 34 | 19 | + | 18 | + | 100.7 | + |
| 35 | 18 | + | 17 | + | 100.6 | + |
| 36 | 22 | + | 19 | + | 101.1 | + |
| 37 | 12 | + | 12 | + | 96.8 | + |
| 38 | 17 | + | 12 | + | 91.0 | + |
| 39 | 20 | + | 17 | + | 101.0 | + |
| 40 | 17 | + | 18 | + | 100.7 | + |
| 41 | 14 | + | 17 | + | 100.8 | + |
| 42 | 13 | + | 10 | + | 93.4 | + |
| 43 | 15 | + | 13 | + | 96.9 | + |
| 44 | 16 | + | 12 | + | 86.9 | + |
| 45 | 13 | + | 11 | + | 99.0 | + |
| 46 | 15 | + | 13 | + | 96.7 | + |

EXAMPLE 6

Preparation of carrier:

Polystyrene beads (diameter: about 6 mm) are dipped overnight in a carbonate buffer (pH 9.5) containing 2.5% glutaraldehyde to treat the surface thereof. The beads are washed lightly with distilled water, and then dipped overnight in a phosphate buffer (pH 7.2) which contains HBc antigen (yHBcAg) produced by an yeast, by which the beads are sensitized. In order to decrease occurrence of nonspecific reaction, the same beads as above are sensitized with bovine serum albumin (BSA).

Reactivities of the sensitized beads to HBc antibody, HBs antibody and HBe antibody were compared with those to human-origin HBc antigen (hHBcAg, a commercially available product).

Comparison with human-origin HBc antigen-sensitized carrier:

(1) Comparison of reactivities to HBc antibody and HBs antibody:

Beads sensitized with yHBcAG and beads sensitized only with BSA were prepared. In order to compare the beads thus prepared with commercially available beads sensitized with hHBcAg, these beads were entered into a tube having an appropriate size, and thereto were added $^{125}$I-labelled HBc antibody or HBs antibody (200 μl), and they were reacted at room temperature overnight. After washing with distilled water, the amount of antibody bound to the beads was measured by counting the radioactivity with a gamma-ray counter. Beads sensitized only with BSA were used as a control. The results are shown in Table 6.

TABLE 6

| Antigen-sensitized beads | Labelled antibody used | |
|---|---|---|
| | HBc antibody | HBs antibody |
| yHBcAg by the present invention | 28,429 | 268 |
| Commercially available hHBcAg | 31,522 | 3,512 |
| BSA | 385 | 139 |

The beads sensitized with yHBcAG showed ten times lower reactivity than that of beads sensitized with hHBcAg in the reactivity to HBs antibody. It will be assumed from the above that yHBcAG was almost not contaminated with HBsAg, but on the other hand, the human-origin HBcAG was contaminated with HBsAg. That is, since the hHBcAg was prepared by using human-origin plasma or liver as the starting material the contaminated HBsAg would not completely be removed by purification thereof. By the way, the reactivity to HBc antibody was not different between them.

Figure 3:
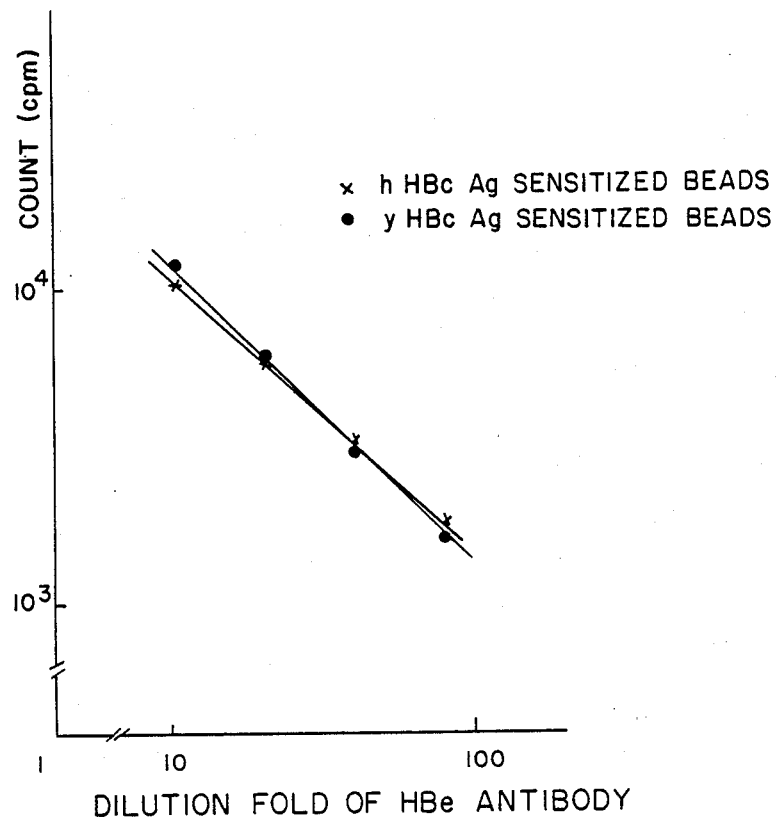
FIG. 3 shows a reactivity of yeast-derived HBcAG-sensitized beads of the present invention against HBe antibody and that of commercially available human-derived HBcAG-sensitized beads.

(2) Comparison of reactivity to HBe antibody:

In order to study whether there is any difference in antigenicity between the HBc antigen expressed in an yeast and the human-origin HBc antigen, the beads sensitized with yHBcAG of the present invention and beads sensitized with hHBcAg were prepared and the reactivity thereof to HBe antibody was tested. The results are shown in the accompanying FIG. 3. As is clear from the figure, both showed almost no difference.

From the above experimental results, it will be clear that the beads sensitized with HBc antigen produced by an yeast can be used instead of beads sensitized with a human-origin HBc antigen for the measurement of HBc antibody by RIA method. It will be apparent that the same or similar results are also obtained in case of EIA method.

What is claimed is:

1. A method for the purification of hepatitis B core antigen which comprises treating a solution containing hepatitis B core antigen which is expressed in a transformed yeast obtained by a DNA recombination technique with an acid, and then subjecting the acid-treated solution to an ion exchange chromatography with an anion exchanger.

2. The method according to claim 1, wherein the acid-treated solution is subjected to salting out with ammonium sulfate before subjecting to the ion exchange chromatography.

3. The method according to claim 1, wherein the starting solution containing hepatistis B core antigen is a crude extract of HBc antigen which is prepared by fracturing recombinant cells by ultrasonic fracture, glass beads fracture, MantonGaulin fracture, or fracturing with a detergent, or a combination of two or more thereof.

4. The method according to claim 1, wherein the treatment of a solution containing hepatistis B core antigen with an acid is carried out by adding an acid to the solution containing HBc antigen and then separating out produced precipitates of lipids and contaminants proteins.

5. The method according to claim 4, wherein the solution containing hepatistis B core antigen is acidified to a pH in the range of not higher than 6 by the addition of an acid.

6. The method according to claim 4, wherein the acid used for the acid treatment is a member selected from the group consisting of hydrochloric acid, sulfuric acid, phosphoric acid, acetic acid and oxalic acid.

7. The method according to claim 1, wherein the anion exchanger used for the ion exchange chromatography is an anion exchanger having diethylaminoethyl group as a functional group thereof.

8. The method according to claim 1, wherein the ion exchange chromatography is carried out by contacting the solution containing hepatitis B core antigen with an anion exchanger which is equilibrated with a buffer having an ion strength of at least 0.001 to adsorb hepatitis B core antigen onto the ion exchanger and then eluting the hepatitis B core antigen with a buffer having an ion strength of 0.01 to 0.5 which is higher than the ion strength of the buffer used for the above equilibration of the ion exchanger.

9. The method according to claim 8, wherein the ion exchange chromatography is carried out by a batch method or a column method.

10. The method according to claim 1, wherein the ion exchange chromatography is combined with a chromatography with a hydroxyapatite.

11. In a method for measuring hepatitis B virus core antibody comprising contacting the sample with a hepatitis B virus core antigen and determining the presence of hepatitis B virus core antibody according to a passive hemagglutination method, an enzyme immunoassay method, or a radioimmunoassay method, wherein the improvement comprises using a purified hepatitis B core antigen obtained by treating a solution containing the hepatitis B core antigen which is expressed in a transformed yeast obtained by a DNA recombination technique with an acid, and then subjecting the acid-treated solution to an ion exchange chromatography with an anion exchanger.

* * * * *